United States Patent [19]
Vojtasek et al.

[11] Patent Number: 6,123,193
[45] Date of Patent: Sep. 26, 2000

[54] SHARPS CONTAINER

[75] Inventors: William J. Vojtasek, Wyomissing; William H. Lape, Reading, both of Pa.

[73] Assignee: Arrow International, Inc., Reading, Pa.

[21] Appl. No.: 09/414,217

[22] Filed: Oct. 7, 1999

[51] Int. Cl.$^7$ .......................... B65D 85/24; B65D 83/10; B23P 19/00; A61M 5/00
[52] U.S. Cl. .............................. 206/366; 29/240; 604/110
[58] Field of Search .................... 206/364–366; 29/240, 240.5; 604/110, 192

[56] References Cited

U.S. PATENT DOCUMENTS

| | | |
|---|---|---|
| 2,567,001 | 9/1951 | Watson . |
| 2,929,510 | 3/1960 | Penn .................................. 206/366 X |
| 2,985,285 | 5/1961 | Riddle . |
| 3,292,776 | 12/1966 | Penn .................................. 206/366 X |
| 4,375,849 | 3/1983 | Hanifl . |
| 4,807,344 | 2/1989 | Velson et al. ............................. 29/240 |
| 4,862,573 | 9/1989 | Velson et al. ............................. 29/240 |
| 5,067,223 | 11/1991 | Bruno .................................. 206/366 X |
| 5,188,598 | 2/1993 | Thead et al. ........................ 206/366 X |
| 5,285,896 | 2/1994 | Salatka et al. . |
| 5,322,165 | 6/1994 | Melker et al. . |
| 5,356,305 | 10/1994 | Latni .................................. 206/366 X |
| 5,368,580 | 11/1994 | Suzuki . |
| 5,395,338 | 3/1995 | Gaba . |
| 5,417,659 | 5/1995 | Gaba . |
| 5,505,705 | 4/1996 | Galpin et al. . |
| 5,531,323 | 7/1996 | Velson et al. ........................... 206/366 |
| 5,533,974 | 7/1996 | Gaba . |
| 5,718,689 | 2/1998 | Stevenson . |
| 5,857,569 | 1/1999 | Hoftman . |

FOREIGN PATENT DOCUMENTS 1120074  12/1961  Germany ............................... 206/366

*Primary Examiner*—Bryon P. Gehman
*Attorney, Agent, or Firm*—Amster, Rothstein & Ebenstein

[57] ABSTRACT

A sharps cup for receiving and storing a plurality of needles against accidental dislodgement, includes a plastic cup defining a bottom, a top, a sidewall connecting the bottom and the top, and a vertically extending central post disposed within and horizontally spaced from the sidewall. A resilient disc is disposed within the cup and defines a plurality of slots and segments, the segments being intermediate the slots, and each segment having a free end spaced from the post. A plastic cover for the cup defines a plurality of needle-receiving passageways therethrough adjacent the post and communicating with spaces between the post and the segment free ends. Each segment free end is individually deflectable toward the bottom adjacent the post by insertion of a needle downwardly through one of the passageways and then into the space intermediate the post and the segment free end. The disc is of a harder material than the needle so that the segment resists withdrawal of the needle by biting into the needle as the segment free end attempts to return from its deflected orientation during withdrawal of the needle.

15 Claims, 3 Drawing Sheets

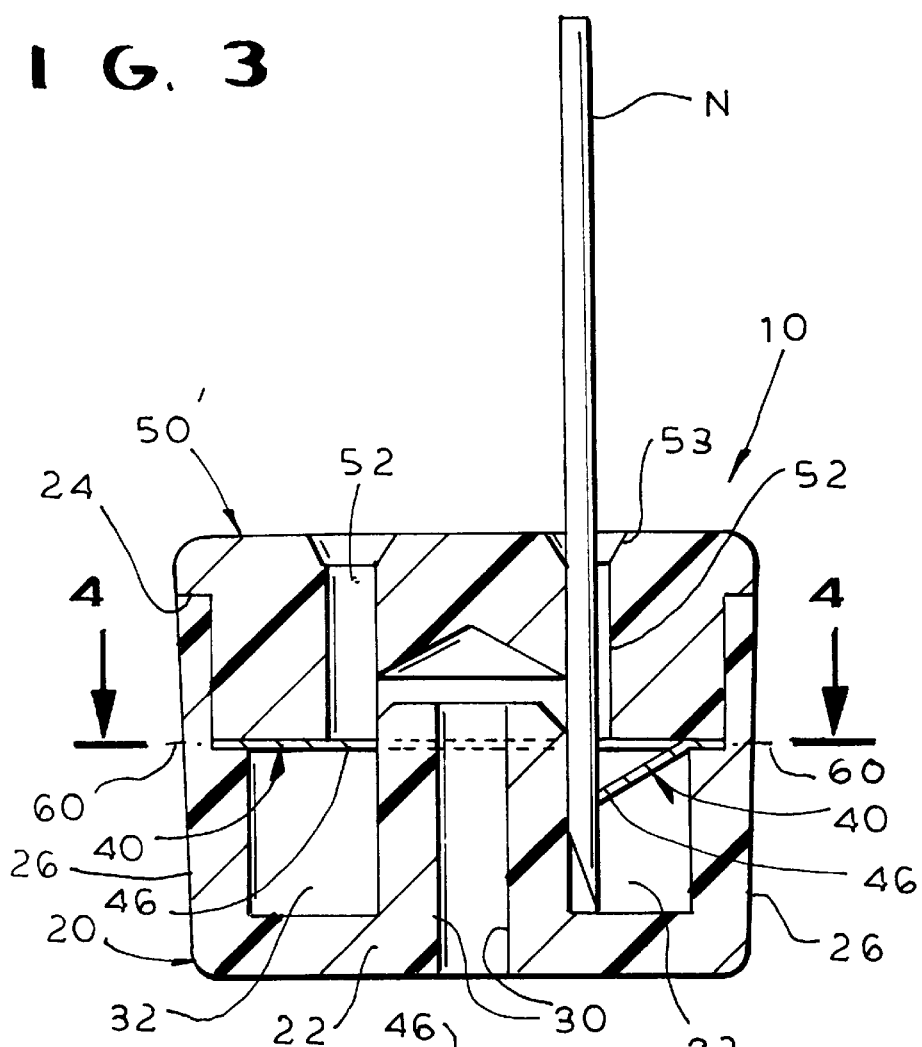

SHARPS CONTAINER

BACKGROUND OF THE INVENTION

The present invention relates to a sharps container, and more particularly to a sharps container which precludes accidental dislodgement of needles therefrom.

The conventional prior art sharps container is a cup of plastic or other puncture-proof material defining a closed bottom, an open top, and a sidewall connecting the bottom and top. A cylinder of compressed foam is snugly fitted within the container so that contaminated needles, sharps and the like may be inserted into the foam and stored there for later disposal. This conventional prior art sharps container has not proven to be entirely satisfactory in use because, while the needles or other sharps placed therein are relatively firmly gripped in a frictional manner by the foam within the container, they remain susceptible to accidental dislodgement if a protruding non-sharp end of a needle or sharp is accidentally contacted (for example, by a nurse's hand in the operating room).

In the attempt to minimize accidental dislodgment of the needles and like sharps from the sharps container, sharps containers have been developed which do not rely upon foam to maintain the needle within the container, but rather trap the needle and a portion of the needle holder—for example, a needle hub or needle securing means—within the container against accidental dislodgement. These sharps containers have not proven to be entirely satisfactory in use, however, as they do not permit the needle or other sharp by itself (without any securing means or hub) to be maintained within the sharps container. As a result, fewer needles or other sharps can be stored in a given sharps container relative to the number which might be stored if it was not necessary to also store the needle hub or other securing mechanism.

Further, some sharps containers have become so complex that the mere downward insertion of a needle thereinto is not sufficient, and the needle must also be moved orthogonally to cause the sharps container to maintain and store the needle.

Accordingly, it is an object of the present invention to provide a sharps container for receiving and storing a plurality of needles against accidental dislodgement therefrom.

Another objective to provide such a sharps container which does not rely on a frictional engagement between the needles and other material within the sharps container.

A further object is to provide such a sharps container which positively grips the needles placed therein.

It is also an object of the present invention to provide such a sharps container wherein a simple downward motion of the needle relative to the sharps container is sufficient to cause receiving and storing of the needle, without the need for any orthogonal movement.

It is another object to provide such a sharps container which is easy and economical to manufacture, use and maintain.

SUMMARY OF THE INVENTION

It has now been found that the above and related objects of the present invention are obtained in a sharps container for receiving and storing a plurality of needles against accidental dislodgement. The sharps container comprises a plastic container defining a bottom, a top, a sidewall connecting the bottom and the top, and a vertically extending central wall disposed within and horizontally spaced from the sidewall. A resilient disc is disposed within the container and defines a plurality of slots and segments, the segments being intermediate the slots, and each segment having a free end spaced from the wall. A plastic cover for the container defines a plurality of needle-receiving passageways therethrough adjacent the wall and communicating with a space between the wall and the segment free ends. Each segment free end is individually deflectable toward the bottom adjacent the wall by insertion of a needle downwardly through one of the passageways and then into the space intermediate the wall and the segment free end. The disc is of a harder material than the needle deflecting the segment free end so that a segment free end resists withdrawal of the needle by biting into the needle as the segment free end attempts to return from its deflected orientation during withdrawal of the needle.

In a preferred embodiment, the slots extend radially outwardly from the wall. The segment free ends are closely disposed about the wall and spaced above the bottom. The segments, in the absence of deflection by a needle, define a generally horizontal plane, and the segment free ends are individually deflectable from the generally horizontal plane towards the bottom adjacent the wall by insertion of needles. The segment free ends are further spaced from the wall when deflected downwardly into the deflected orientation by needles than when in a generally horizontal plane and not deflected downwardly by needles. The segment free ends are deflected downwardly by the needles to an angle of 16–46° from a generally horizontal plane.

Preferably the cover is configured and dimensioned to be received atop the container, and the passageways are tapered downwardly and disposed along a circumference of the cover. Preferably, the container is a plastic cup, the cover is a plastic cover for the cup, and the wall is a central post within the cup.

In a preferred embodiment, the cover includes means for deflecting the segment free ends downwardly, and the segment free ends, in the absence of deflection by needles, extend downwardly at a slight angle (preferably about 10° from the horizontal) to provide slots of appreciable width therebetween and minimize accidental overlapping of adjacent segment free ends.

BRIEF DESCRIPTION OF THE DRAWINGS

The above and related objects, features and advantages of the present invention will be more fully understood by reference to the following detailed description of the presently referred, albeit illustrative, embodiments of the present invention when taken in conjunction with the accompanying drawing wherein:

FIG. 3 is a sectional view thereof, with the needle inserted thereinto;

FIG. 4 is a sectional view thereof taken along the line 4—4 of FIG. 2; and.

DETAILED DESCRIPTION OF THE PREFERRED EMBODIMENTS

Figure 1:
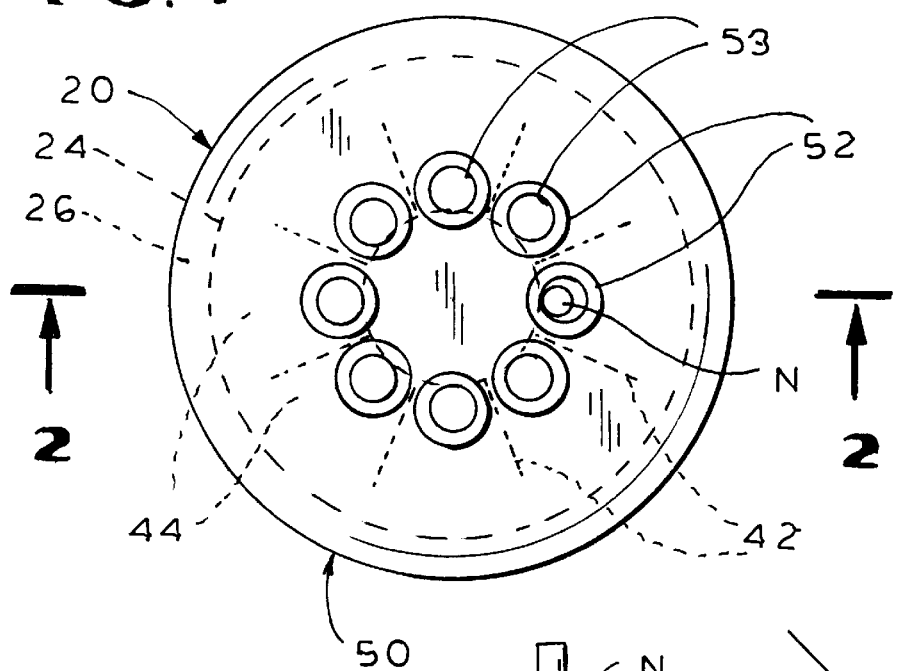
FIG. 1 is a top plan view of a sharps container according to the resent invention and a needle about to be inserted thereinto.
Figure 2:
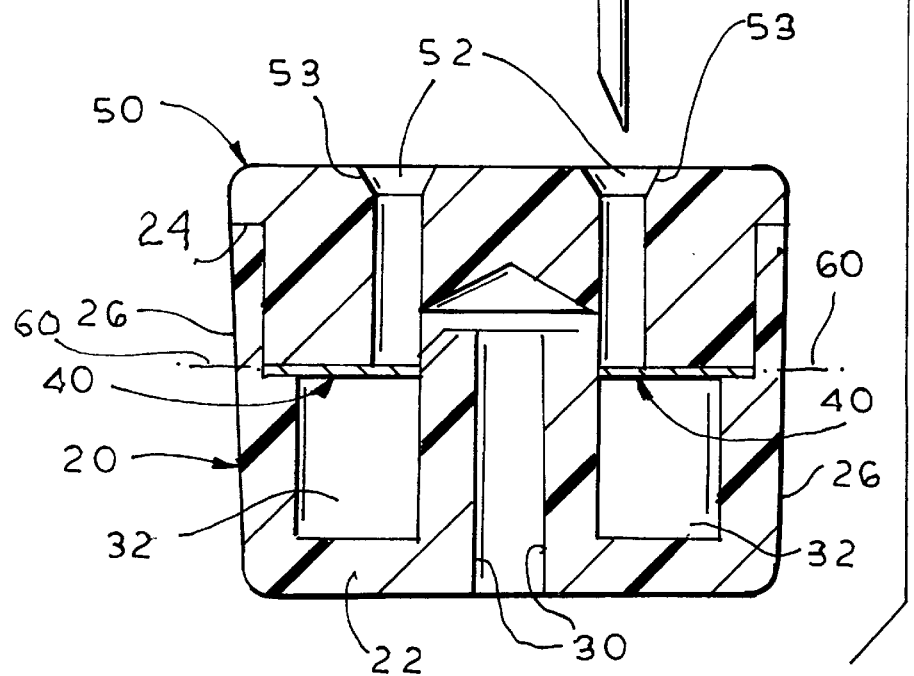
FIG. 2 is a sectional view thereof taken along the line 2—2 of FIG. 1.

Referring now to the drawing, and in particular to FIGS. 1 and 2 thereof, therein illustrated is a sharps container according to the present invention, generally designated by the reference numeral 10. The sharps container 10 is capable of receiving and storing a plurality of needles N against accidental dislodgement (for example, through accidental brushing of the protruding portion of the needle, such as might be occasioned by a nurse in the operating room). A single needle N is shown ready for insertion into the sharps container 10.

The sharps container 10 comprises a plastic container, generally designated 20, defining a bottom 22, a top 24, and a sidewall 26 connecting the bottom 22 and the top 24. Preferably the container bottom 22 is closed, while the container top 24 is at least partially opened. A vertically extending central wall, preferably in the nature of a central post 30, preferably integrally formed with the container bottom 22, is disposed within and horizontally spaced from the sidewall 26, thereby to define a space 32 intermediate the wall 30 and the sidewall 26. As illustrated, the plastic container 20 is cylindrical in plan, but clearly other configurations could be used—for example, a downwardly tapering configuration or a polygonal configuration.

The plastic container 20 may be integrally formed (as illustrated) or the bottom 22 may be removable from the top 24 and sidewall 26. The removability of the bottom 22 and the wall 30 integral therewith enables eventual intentional separation of the needles from the container 10. The sidewall 26 may be opaque or transparent to enable visualization of the needle retention mechanism.

A resilient disc, generally designated 40, is disposed within the container 20 and, as best seen in FIG. 4, defines a plurality of slots 42 and segments 44. Each segment 44 is disposed intermediate an adjacent pair of slots 42 and has a free end 46 which extends inwardly towards the wall 30, but is slightly spaced from the wall 30 (e.g., about 0.127 mm (0.005 inch) clearance, not clearly noticeable in the drawing). The segments 44 are disposed about the wall 30, and at least the free ends 46 thereof are spaced above the cup bottom 22, thereby to enable deflection downwardly of the segment free ends 46 into the space 32. In a preferred embodiment the slots 42 extend radially outwardly from the aligned peripheral areas of the wall 30.

Figure 5:
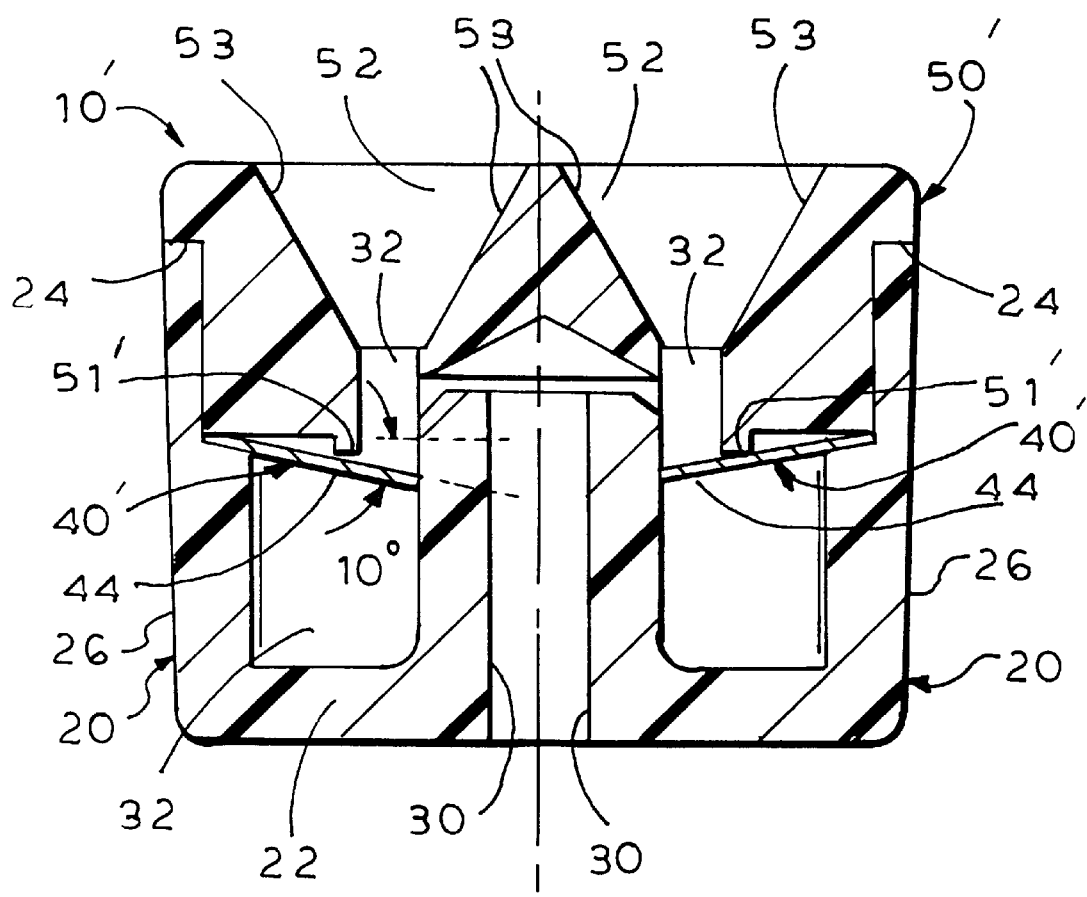
FIG. 5 is a sectional view, similar to FIG. 2 of a second embodiment.

A plastic cover, generally designated 50, for the container 20 defines a plurality of needle-receiving passageways 52 therethrough adjacent the wall 30 and communicating with the space 32 between the wall 30 and the segments free ends 46. Preferably the cover 50 is configured and dimensioned to be received atop of container 20 and to substantially close the open top 24 thereof. The passageways 52 may be of cylindrical cross section or include a portion 53 which tapers downwardly and inwardly to assist in directing the needles through the passageways 52 and into the desired areas within the container 20. The downward and inward taper may be short so that the portion 53 is of generally the same diameter as the passageway 52 (as illustrated in FIGS. 2 and 3 of the first embodiment 10) or the taper may occupy a greater portion of the cover 50', thereby presenting a more easily approachable opening into space 32 from the top of the cover 50' (as illustrated in FIG. 5 for a second embodiment 10'). In the second embodiment 10' it is easier for the needle to be placed into the passageway 52 of the sharps container.

As illustrated, the passageways 52 are disposed at regular intervals along a circumference of the cover 50. Clearly, the passageways 52 may be disposed in different patterns, although the circumferential disposition provides a maximum utility of the available space. The configuration and dimensions of the passageways 52 may vary with the intended applications so as to accommodate the particular sharps which will be inserted into the container 10. The circumference along which the passageways 52 are disposed is adjacent the walls 30 and typically well spaced from the sidewall 26.

Referring now to FIGS. 3 and 4 in particular, where the needle N is shown in its final position within sharps container 10, each segment free end 46 is individually deflectable towards the bottom 22 adjacent to wall 30 by insertion of a needle (or other sharp) downwardly through one of the passageways 52 and then into the space 32 intermediate the wall and the adjacent segment free end 46. In particular applications, the outer circumference of the wall 30 may be provided with vertically extending recesses or grooves (not shown) capable of partially receiving and guiding the needles during the insertion procedure.

The segments 44, in the absence of deflection by needles, define a generally horizontal plane 60. The segment free ends 46 are individually deflectable from that generally horizontal plane 60 towards the bottom 22 adjacent to wall 30 by the insertion of needles. The segment free ends 46 are preferably deflected downwardly by 27-15 gage needles to an angle of 16–46°, respectively, from the generally horizontal plane 60, and optimally an angle of about 31°. The segment free ends 46 are further spaced from the wall 30 when in the deflected orientation than when in the generally horizontal plane 60 (i.e., when not deflected downwardly by needles).

It is critical that the disc 40 be made of a harder material than the needles N (or like sharps) being inserted into the sharps containers 10. Thus, after the inserted needle deflects a segment free end 46, the segment 44 resists withdrawal of the needle from the container 20 by biting into the needle as the segment free end 46 attempts to return from its deflected orientation during withdrawal of the needle. This biting provides positive locking of the actual needle by the sharps container 10, and not merely an engagement or blockage of a needle hub or a needle holder. As the needles and like sharps are typically made of stainless steel, various spring metals harder than stainless steel may be used for the disc 40—for example, 1095 Spring Steel (Blue Temper) from Lyon Industries.

The sharps container 10 of the present invention maximizes the number of needles that may be stored in a given sharps container because the needles alone are received and maintained by the sharps container, without any need for spacing the needles apart so as to allow for a needle hub or other needle holder therebetween. The number of needles N receivable with a given sharps container 10 is equal to the number of passageways 52, the latter preferably being equal to the number of segments 44.

The sharps container 10 of the present invention retains the needles inserted thereinto against accidental dislodgement not through a frictional engagement, but rather through an actual interlocking engagement resulting from the harder spring material of disc segment free end 46 entering into ("biting") the softer material of the needle. It will be appreciated that, as a general rule, the resiliency of the deflected segment free end 46 is itself insufficient to cause the segment free end 46 to bite even into the softer material of a needle. Rather it is the upward manually force initially applied to the needle during an accidental dislodgement thereof which forces the segment free end 46 to attempt to enter into the space occupied by the needle and thus bite into the needle. Accordingly, the extent of the biting is generally proportional to the force tending to accidentally dislodge the needle. (The resiliency of the segment 44 is used to retain the needle within the container 10 only when there is no force tending to accidentally dislodge the needle therefrom.)

It will be understood that, while the present application describes and shows the sharps as needles, clearly other sharps are also encompassed by the term "needles" as used herein.

Referring now to FIG. 5 in particular, in a second embodiment of the present invention, generally designated 10', the cover 50' defines passageways 52 which are larger at the top than in the first embodiment 10, thus facilitating placement of the needles into the container 10'. Additionally, the cover 50' defines a downwardly extending lug at 51' which bears downwardly on the segments 44. Preferably the lugs 51' force the segment free ends 46 to deflect downwardly about 10° even before any insertion of a needle. The initial downward and inward deflection of the segment free ends 46 insures proper operation of the disc 40'.

For economic reasons, the disc 40' is preferably made by a punch and die operation, and such a punch and die operation typically results in substantially no clearance between adjacent segments 44. Without any clearance or gap between adjacent segments, adjacent segments tend to overlap each other upon deflection by needles N, thereby making it more difficult to insert the needles into the sharps container 10'. The second embodiment 10' obtains the benefits of the economical punch and die process while avoiding or at least minimizing the potential overlapping of adjacent segments due to the absence of any gap between the segments. Instead of the segments 44 initially being in a horizontal plane 60 (as illustrated in FIG. 2 for the first embodiment 10), the segment free ends 46 of the second embodiment 10' are initially deflected downwardly (for example, preferably about 10°) by downwardly protruding lugs 51' of the cover 50' (as illustrated in FIG. 5 for the second embodiment 10'). The slight initial deflection of the segment free ends 46 introduces or enlarges any gap between the segments 44 and thereby decreases the likelihood of any adjacent segments overlapping one another upon deflection.

To summarize, the present invention provides a sharps container for receiving and storing a plurality of needles against accidental dislodgement thereof, without relying on a frictional engagement between the needles and other materials of a sharps container, but rather positively gripping the needles placed therein against accidental dislodgement. The needle is inserted by a simple downward motion relative to the sharps container, without the need for any orthogonal movement. The sharps container is easy and economical to manufacture, use and maintain.

Now that the preferred embodiments have been shown and described in detail, various modifications and improvements thereon will become readily apparent to those skilled in the art. Accordingly, the spirit and scope of the present invention is to be construed broadly and limited only by the appended claims, and not by the foregoing specification.

What is claimed is:

1. A sharps container for receiving and storing a plurality of needles against accidental dislodgement, comprising;
   (A) a container defining a bottom, a top, a sidewall connecting said bottom and said top, and a vertically extending wall disposed within and horizontally spaced from said sidewall;
   (B) a resilient disc disposed within said container and defining a plurality of slots and segments, said segments being intermediate said slots, and each said segment having a free end spaced from said wall; and
   (C) a cover for said container defining a plurality of needle-receiving passageways therethrough adjacent said wall and communicating with a space between said wall and said segment free ends;
   each said segment free end being individually deflectable toward said bottom adjacent said wall by insertion of a needle downwardly through one of said passageways and then into the space intermediate said wall and said segment free end;
   said disc being of a harder material than the needle deflecting said segment free end so that said segment resists withdrawal of the needle by biting into the needle as said segment free end attempts to return from its deflected orientation during withdrawal of the needle.

2. The sharps container of claim 1 wherein said slots extend radially outwardly from said wall.

3. The sharps container of claim 1 wherein said segments, in the absence of deflection by a needle, define a generally horizontal plane, and said segment free ends are individually deflectable from the generally horizontal plane towards said bottom adjacent said wall by insertion of needles.

4. The sharps container of claim 1 wherein said segment free ends are further spaced from said wall when deflected downwardly into the deflected orientation by needles than when in a generally horizontal plane and not deflected downwardly by needles.

5. The sharps container of claim 1 wherein said segment free ends are deflected downwardly by needles to an angle of 16–46° from a generally horizontal plane.

6. The sharps container of claim 1 wherein said segment free ends are closely disposed about said wall and spaced above said bottom.

7. The sharps container of claim 1 wherein said container passageways are disposed along a circumference of said cover.

8. The sharps container of claim 1 wherein said cover is configured and dimensioned to be received atop of said container, and said passageways are tapered inwardly and downwardly.

9. The sharps container of claim 1 where said container is a plastic cup and said cover is a plastic cover for said cup.

10. The sharps container of claim 1 wherein said wall is a central post.

11. The sharps container of claim 1 wherein said segment free ends, in the absence of deflection by needles, extend downwardly at a slight angle to provide slots of appreciable width therebetween and minimize accidental overlapping of adjacent segment free ends.

12. The sharps container of claim 11 wherein said slight angle is about 10° from the horizontal.

13. The sharps container of claim 12 wherein said cover includes means for deflecting said segment free ends downwardly.

14. A sharps cup for receiving and storing a plurality of needles against accidental dislodgement, comprising;
   (A) a plastic cup defining a bottom, a top, a sidewall connecting said bottom and said top, and a vertically extending central post disposed within and horizontally spaced from said sidewall;
   (B) a resilient disc disposed within said cup and defining a plurality of slots and segments, said slots extending radially outwardly from said post, said segments being intermediate said slots, and each said segment having a free end closely disposed adjacent said post, spaced from said post and spaced above said bottom, each said segment free end being deflectable downwardly by a needle to an angle of 16–46° from a generally horizontal plane; and (C) a plastic cover for said cup defining a plurality of needle-receiving passageways therethrough adjacent said post and communicating with a space between said post and said segment free ends, said cover being configured and dimensioned to be received atop of said cup, and said passageways being tapered downwardly and inwardly;

said segments in the absence of deflection by a needle, defining a generally horizontal plane, each said segment free end being individually deflectable from the generally horizontal plane toward said bottom adjacent said post by insertion of a needle downwardly through one of said passageways and then into the space intermediate said post and said segment free end;

each said segment free end being further spaced from said post when deflected downwardly into the deflected orientation by a needle than when in the generally horizontal plane and not deflected downwardly by a needle;

said disc being of a harder material than the needle deflecting said segment free end so that said segment resists withdrawal of the needle by biting into the needle as said segment free end attempts to return from its deflected orientation during withdrawal of the needle.

15. The sharps cup of claim 14 wherein said cover includes means for deflecting said segment free ends downwardly, and said segment free ends, in the absence of deflection by needles, extend downwardly at a slight angle of about 10° from the horizontal to provide slots of appreciable width therebetween and minimize accidental overlapping of adjacent segment free ends.

* * * * *